United States Patent
Sakaguchi (10) Patent No.: US 9,566,199 B2
(45) Date of Patent: Feb. 14, 2017

(54) DISPOSABLE DIAPER

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/387,800

(22) PCT Filed: Mar. 28, 2013

(86) PCT No.: PCT/JP2013/059340
§ 371 (c)(1),
(2) Date: Sep. 24, 2014

(87) PCT Pub. No.: WO2013/147061
PCT Pub. Date: Oct. 3, 2013

(65) Prior Publication Data
US 2015/0073376 A1    Mar. 12, 2015

(30) Foreign Application Priority Data

Mar. 30, 2012  (JP) ................................. 2012-083047

(51) Int. Cl.
*A61F 13/15* (2006.01)
*A61F 13/56* (2006.01)
(Continued)

(52) U.S. Cl.
CPC ....... *A61F 13/5644* (2013.01); *A61F 13/5633* (2013.01); *A61F 13/581* (2013.01); *A61F 13/622* (2013.01)

(58) Field of Classification Search
CPC .............. A61F 13/5622; A61F 13/5644; A61F 13/581; A61F 13/622
See application file for complete search history.

(56) References Cited

U.S. PATENT DOCUMENTS 6,276,032 B1 *  8/2001  Nortman ............ A44B 18/0065
                                                          24/572.1
7,189,220 B2    3/2007  Miyoshi et al.
(Continued)

FOREIGN PATENT DOCUMENTS

CN    1496726 A    5/2004
CN    1819813 A    8/2006
(Continued)

OTHER PUBLICATIONS

Notification of Reasons for Rejection dated Feb. 2, 2013 in corresponding Japanese Application No. 2012-083047, filed Mar. 30, 2013.
(Continued)

*Primary Examiner* — Bradley Philips
(74) *Attorney, Agent, or Firm* — Hauptman Ham, LLP (57) ABSTRACT

The fastening tape included in the disposable diaper has a base sheet, and a hook sheet provided with a plurality of engagement hooks and fixed on the base sheet. The engagement strength of the fastening tape is 0.3 N/30 mm or more, and 1.5 N/30 mm or less. The bending rigidity value in the direction in which the surface of the base sheet of the fastening tape comes close is smaller than the bending rigidity value in the direction in which the surface of the hook sheet of the fastening tape comes close.

17 Claims, 5 Drawing Sheets

(51) Int. Cl.
*A61F 13/62* (2006.01)
*A61F 13/58* (2006.01)

(56) References Cited

U.S. PATENT DOCUMENTS

| | | | |
|---|---|---|---|
| 7,407,496 | B2 | 8/2008 | Petersen |
| 7,578,813 | B2 | 8/2009 | Mitsui et al. |
| 7,749,213 | B2 | 7/2010 | Mitsui et al. |
| 2002/0099352 | A1 | 7/2002 | Heden et al. |
| 2004/0068848 | A1* | 4/2004 | Ausen ............... A44B 18/0049 24/452 |
| 2005/0033257 | A1 | 2/2005 | Miyoshi et al. |
| 2011/0015608 | A1* | 1/2011 | Fujioka ............ A61F 13/15731 604/389 |
| 2011/0040274 | A1 | 2/2011 | Kline et al. |
| 2011/0313389 | A1* | 12/2011 | Wood ................ A44B 18/0065 604/391 |

FOREIGN PATENT DOCUMENTS

| | | |
|---|---|---|
| EP | 0974326 B1 | 7/1998 |
| EP | 1652502 A1 | 5/2006 |
| EP | 2810631 A1 | 12/2014 |
| JP | 09-299397 A | 11/1997 |
| JP | 2004-057413 A | 2/2004 |
| JP | 2005-7159 A | 1/2005 |
| JP | 2009-082484 A | 4/2009 |
| JP | 2012-050717 A | 3/2012 |
| TW | 200412914 | 8/2004 |
| TW | 200509867 A | 3/2005 |
| TW | 2009-42216 A | 10/2009 |
| TW | M413477 U1 | 10/2011 |
| WO | 2011/040042 A1 | 4/2011 |

OTHER PUBLICATIONS

Search Report of Taiwanese Patent Application No. 102111222 mailed Feb. 12, 2014.
Notification of First Office Action in Chinese Application No. 201380000988.5 dated Mar. 6, 2014.
International Search Report mailed Jun. 25, 2013 in International Patent Application No. PCT/JP2013/059340 filed Mar. 28, 2013.
Extended European Search Report dated Nov. 4, 2015, corresponding to European Patent Application No. 13769970.8.
Office Action in EA Patent Application No. 201401050, dated Jun. 7, 2016.
Office Action in GCC Patent Application No. GC2013-23951, mailed on Aug. 7, 2016.

* cited by examiner

DISPOSABLE DIAPER

RELATED APPLICATIONS

The present application is a National Phase of International Application Number PCT/JP2013/059340, filed Mar. 28, 2013, which claims priority to Japanese Application Number 2012-083047, filed Mar. 30, 2012.

TECHNICAL FIELD

The present invention relates to a disposable diaper with a fastening tape to one of a front waistline unit and back waistline unit.

BACKGROUND ART

In the conventional art, as a disposable diaper used mainly in an infant and toddler and the like, there is provided a so called open-type disposable diaper provided with a fastening tape for fastening at side flaps of a back waistline unit thereof.

In such an open-type disposable diaper, a structure of a fastening tape is known in which the rigidity of the tip of the fastening tape is lower than the rigidity of the proximal end of the fastening tape (for example, Patent Literature 1). According to a fastening tape with such a structure, even when the wearer of the disposable diaper moves, the tip of the fastening tape easily becomes deformed with following the change in the shape of the body of the wearer, which makes it difficult for the fastening tape to unfasten from the disposable diaper.

CITATION LIST

Patent Literature

[PTL 1]
Japanese Unexamined Patent Application Publication No. 2005-007159 (FIG. 1)

SUMMARY OF INVENTION

Technical Problem

However, the aforementioned conventional disposable diaper had the following problems. In other words, the shape of the waistline of the wearer, especially, of an infant and toddler, varies largely before and after breathing and eating. More specifically, the waistline of the wearer is the portion where the irregularities are often found and the changes in the size of the abdomen due to breathing and eating, as well as the changes in the shape of the portion around the flank due to the movement of legs are remarkable.

When a disposable diaper is worn on such a body of a wearer, a lot of efforts are required for making fine adjustments of the position at which the fastening tape is secured by attaching and detaching the fastening tape in order to secure the fastening tape at an appropriate position without over-tightening the waistline of the wearer. On the other hand, by increasing the rigidity of the fastening tape, the fastening tape can firmly support the disposable diaper, which makes it difficult for the position of the disposable diaper to be shifted, but gives rise to another problem in that the portion around the fastening tape cannot follow the complex shape of the waistline of the wearer.

Thus, the present invention has been achieved in view of such a situation, and an object thereof is to provide a disposable diaper that can more appropriately run along the shape of the waistline of the wearer without over-tightening the waistline of the wearer.

Solution to Problem

An aspect of the present invention is summarized as a disposable diaper (disposable diaper 10) including: a vertically long absorbent body (absorbent body 15) which is formed by a front waistline unit (front waistline unit 20), a back waistline unit (back waistline unit 40), and a crotch unit (crotch unit 30) and which including a liquid-retentive absorber (absorber 35); side flaps (50) provided at least at a part of the side edges of the absorbent body in a product widthwise direction; and a fastening tape (fastening tape 100) attached to the side flap, extending outside in the product widthwise direction of the absorbent body from one of the front waistline unit and the back waistline unit, and configured to be fastened to a remaining one of the front waistline unit and the back waistline unit; wherein the fastening tape has a base sheet (base sheet 120), and a hook sheet (hook sheet 110) provided with a plurality of engagement hooks (engagement hooks 111) and fixed on the base sheet; the engagement strength of the fastening tape is 0.3 N/30 mm or more, and 1.5 N/30 mm or less; and the bending rigidity value in a direction in which a surface of the base sheet of the fastening tape comes close is smaller than the bending rigidity value in a direction in which a surface of the hook sheet of the fastening tape comes close.

Advantageous Effects of Invention

According to the features of the present invention, it is possible to provide a disposable diaper that can more appropriately run along the shape of the waistline of the wearer without over-tightening the waistline of the wearer.

DESCRIPTION OF EMBODIMENTS

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Schematic Shape of Disposable Diaper

Figure 1:
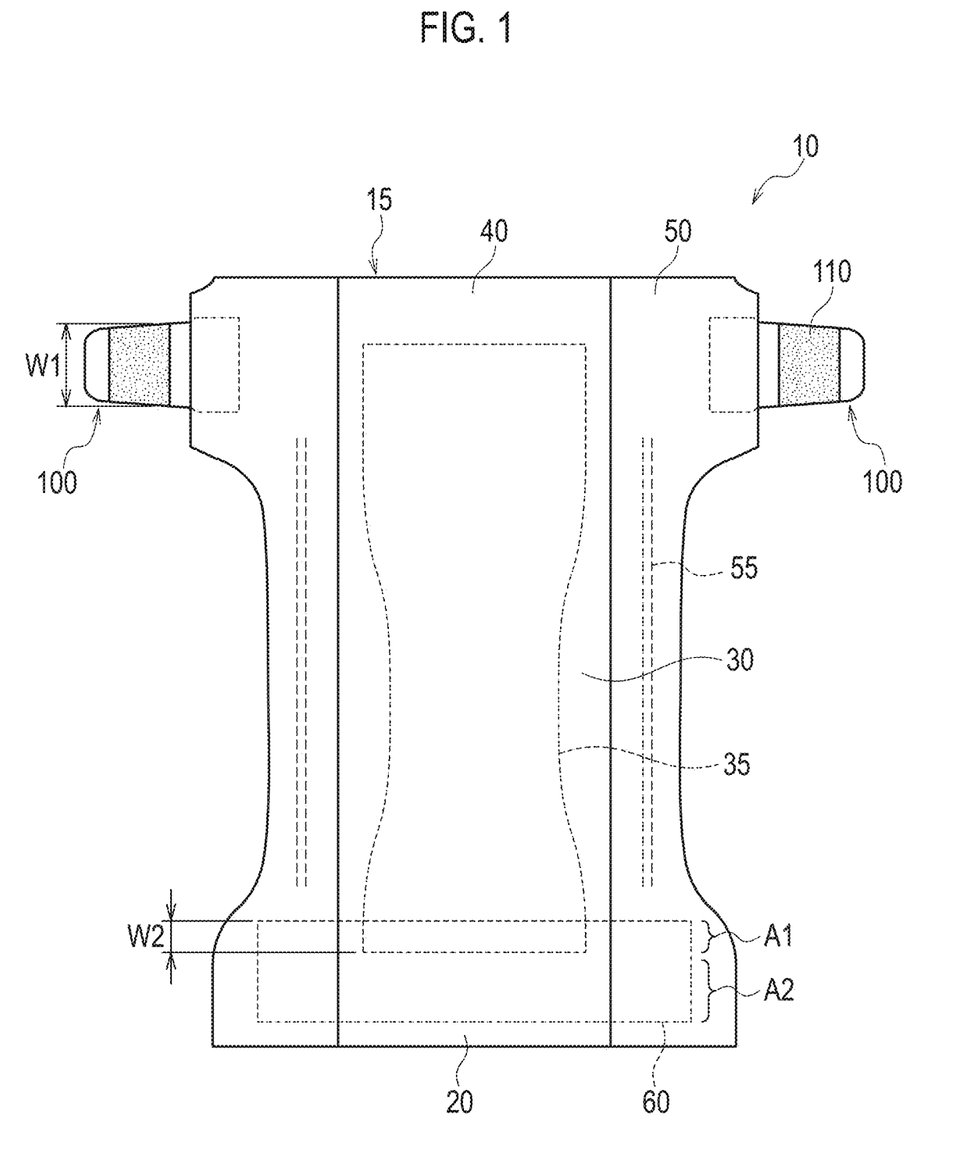
FIG. 1 is a plan view of a disposable diaper 10 according to an embodiment of the present invention.

FIG. 1 is a plan view of a disposable diaper 10 according to the present embodiment. As shown in FIG. 1, the disposable diaper 10 is an open-type diaper having a front waistline unit 20, a crotch unit 30, and a back waistline unit 40. The target persons by whom the disposable diaper 10 can be used are not particularly limited, but for example, the disposable diaper, specifically, can be favorably used by infants and toddlers.

An absorbent body 15 is configured by the front waistline unit 20, the crotch unit 30, and the back waistline unit 40. The absorbent body 15 has a vertically long shape including a liquid-retaining absorber 40. In the present embodiment, the absorber 35 is provided across the front waistline unit 20, the crotch unit 30, and the back waistline unit 40. The absorber 35 has a shape such that the width of the absorber in the central portion of the product longitudinal direction $D_L$ of the absorbent body 15 is narrow. The shape of the absorber 35 is not limited to the shape shown in FIG. 1, and may also be a simple rectangle. Furthermore, the absorber 35 must at least be provided in the crotch unit 30.

The absorbent body 15 is similar to the conventional open-type disposable diaper, and can be configured appropriately by using well-known members and material. Furthermore, the absorbent body 15 may also include a liquid-permeable topsheet, solid gathers provided in the side edges of the absorbent body 15 along the longitudinal direction $D_L$, and waist gathers provided in the back waistline unit 40 along the widthwise direction $D_W$, which are not shown in the figure.

Side flaps 50 are provided in the side edges in the widthwise direction $D_W$ of the absorbent body 15. The side flaps 50 are configured by one layer of nonwoven fabric or two or more plurality of layers of nonwoven fabric layered on each other.

In the present embodiment, the side flaps 50 are provided across the entire region of the absorbent body 15 in the product longitudinal direction $D_L$. That is, the side flaps 50 are provided from the front waistline unit 20 up to the back waistline unit 40. The width of the side flaps 50 corresponding to the crotch unit 30 is less than the width of the side flaps 50 corresponding to the front waistline unit 20 and the back waistline unit 40. The side flaps 50 need not necessarily be provided across the entire region of the absorbent body 15 in the product longitudinal direction $D_L$, for example, the side flaps may be provided only in the region corresponding to the back waistline unit 40.

Furthermore, in the side edges in the product widthwise direction $D_W$ of the absorbent body 15, specifically, in the side flaps 50, leg elastic members 55 stretchable along the product longitudinal direction $D_L$ of the absorbent body 15 are provided. The absorbent body 15 is contracted in the longitudinal direction $D_L$ by the leg elastic members 55. The absorbent body 15 thus contracted can be, particularly, elongated in the product longitudinal direction $D_L$ by Leg elastic member 55.

A fastening tape 100 is installed in the side flaps 50. Specifically, the fastening tape 100 extends towards the outer side in the product widthwise direction $D_W$ of the absorbent body 15 from the back waistline unit 40. The fastening tape 100 is configured to be secured to the front waistline unit 20. Specifically, a hook sheet 110 (see FIG. 2) of the fastening tape 100 is configured to engage with a target tape 60 provided at a backsheet 70 (not shown in FIG. 1; see FIG. 5) side of the front waistline unit 20.

The fastening tape 100 may be installed in the side flaps 50 so as to extend towards the outer side in the product widthwise direction $D_W$ of the absorbent body 15 from the front waistline unit 20, rather than the back waistline unit 40, but in the case of infants and toddlers for whom the disposable diaper is changed mostly while lying in the supine state, the fastening tape 100 is desired to be installed in the back waistline unit 40.

(2) Shape of Fastening Tape

Figure 2:
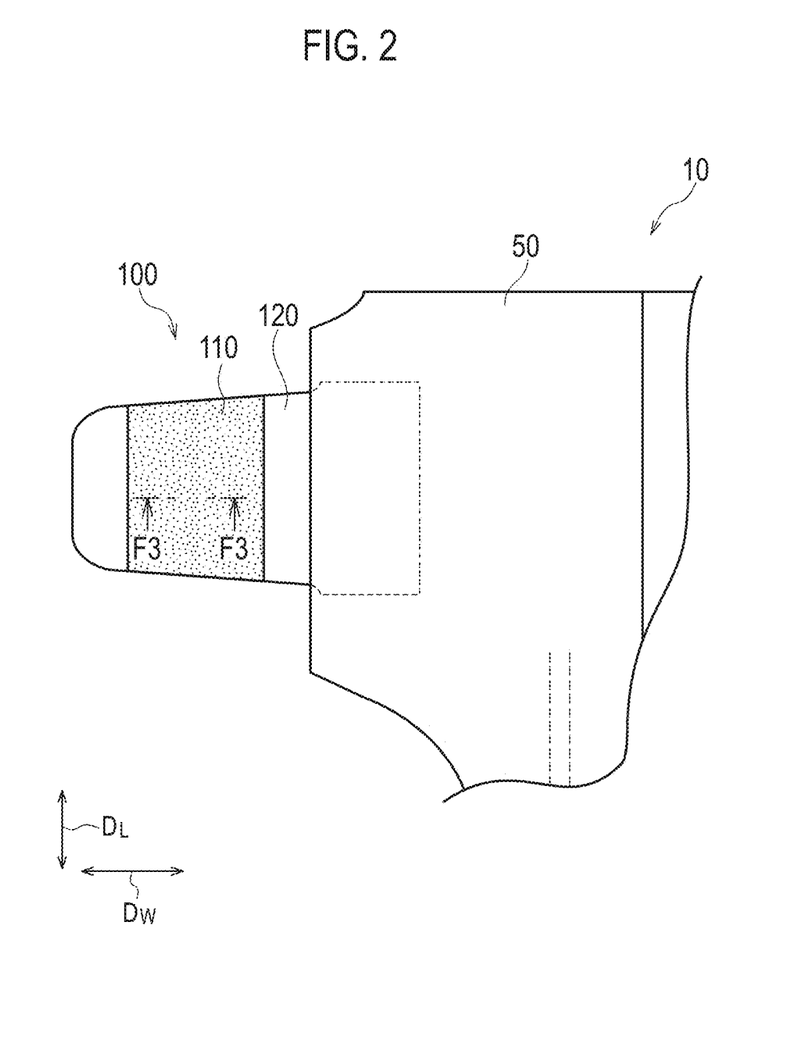
FIG. 2 is an enlarged view of a fastening tape 100 portion of the disposable diaper 10 according to the embodiment of the present invention.
Figure 3:
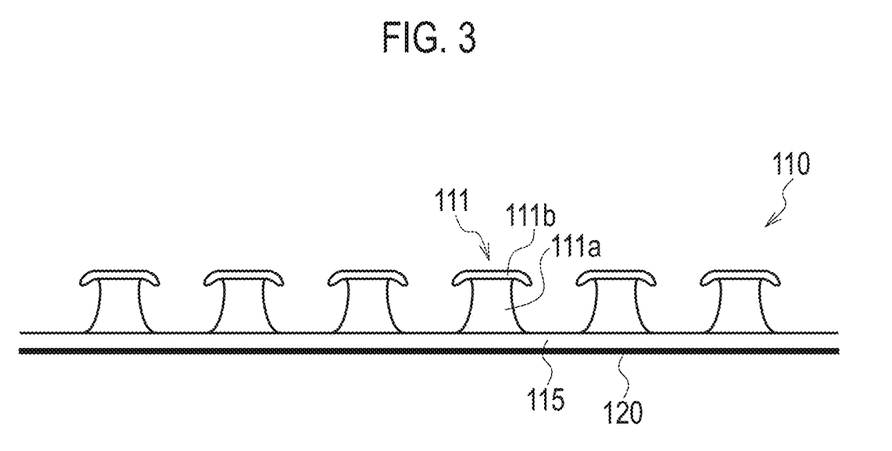
FIG. 3 is an enlarged cross-sectional view of a hook sheet 110 along an F3-F3 line of FIG. 2.

Next, the shape of the fastening tape 100 is described with reference to FIG. 2 and FIG. 3. FIG. 2 is an enlarged view of the fastening tape 100 portion of the disposable diaper 10. FIG. 3 is an enlarged cross-sectional view of the hook sheet 110 along the F3-F3 line of FIG. 2.

As shown in FIG. 2 and FIG. 3, the fastening tape 100 is installed in the region of the side flaps 50 corresponding to the back waistline unit 40 (see FIG. 1). The fastening tape 100 has the hook sheet 110 provided with a plurality of engagement hooks 111 and a base sheet 120 made of nonwoven fabric. In addition, the base sheet 120 may be obtained by laminating a film on nonwoven fabric.

Furthermore, the hook sheet 110 has a base sheet unit 115, and a plurality of engagement hooks 111 rising from the surface of the base sheet unit 115. The engagement hooks 111 have an umbrella unit 111$b$, and a pillar unit 111$a$ that is narrower than the umbrella unit 111$b$, is positioned towards a base sheet 120, and rises from the base sheet unit 115.

The hook sheet 110 is joined with the base sheet 120. The hook sheet 110 and the base sheet 120 are desired to be joined such that the stiffness of the fastening tape 100 does not become more than necessary. Specifically, the hook sheet 110 and the base sheet 120 are desired to be joined with a hot-melt adhesive applied intermittently in dot shape, line shape, or spiral shape. The hook sheet 110 and the base sheet 120 may also be joined with a heat seal and the like.

Furthermore, in order to reduce the rigidity of the hook sheet 110, various well-known methods, such as reducing the thickness of the base portion of the hook sheet 110, and increasing the gap of the base portion, can be used.

The base sheet 120 is made of one or two or more sheets overlapping one another, specifically, nonwoven fabric or sheets obtained by laminating a film on nonwoven fabric, or the like. As the base sheet 120, it is possible to use a sheet obtained by laminating a thermoplastic film on various types of nonwoven fabric such as nonwoven fabric or spunbond (SB) which is manufactured using a manufacturing method such as spunbond, spunbond-meltblown-spunbond (SMS), and through air.

The base sheet 120, specifically, may have a configuration in which two or more sheets are overlapping one another. In such a case, the basis weight per one nonwoven fabric sheet is between 10 and 80 g/m², preferably between 15 and 60 g/m², and more preferably between 20 and 55 g/m². The total thickness of the base sheet 120 is between 150 μm and 550 μm, as described above, and preferably between 250 μm and 500 μm. In addition, the thickness of the nonwoven fabric has been measured using a thickness indicator (a thickness indicator manufactured by TESTER SANGYO Co., Ltd.) in which a measurement terminal has a circular shape (5-mm radius) and a load is 1.23 N.

Also, when the base sheet 120 is made of two or more layers of nonwoven fabrics, it is preferable that the nonwoven fabrics are joined with one another in the form of a net-shaped pattern using an adhesive of 2 g/m² to 8 g/m².

(3) Characteristics of Fastening Tape 100

Figure 4:
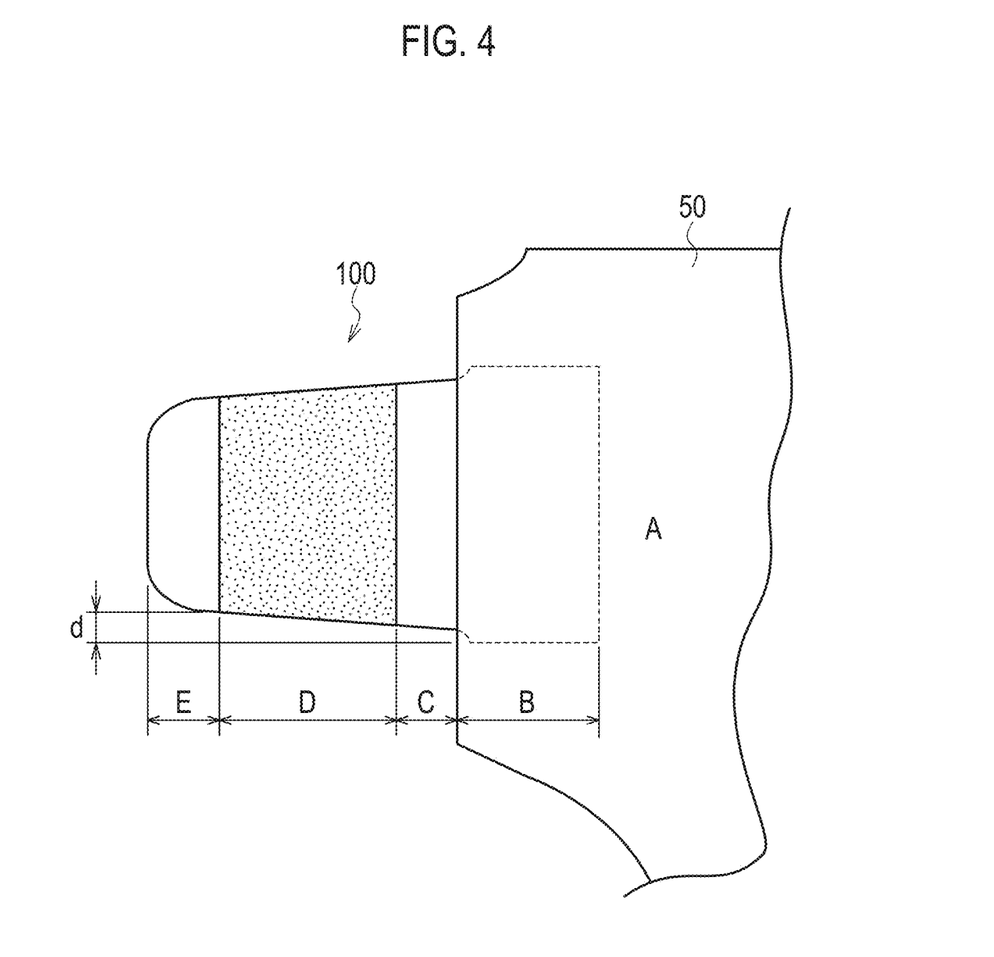
FIG. 4 is a diagram illustrating a region in side flaps 50 and the fastening tape 100 according to the embodiment of the present invention.

The characteristics of the fastening tape 100 having the above-described structure, specifically, the bending rigidity and engagement strength of the fastening tape 100 will be described. FIG. 4 is a diagram illustrating a region in the side flaps 50 and the fastening tape 100.

As illustrated in FIG. 4, in the present embodiment, the fastening tape 100 is divided into a proximal region B, a central region C, a hook sheet region D, and a tip region E. Furthermore, the portion of the side flaps 50 that is adjacent to the proximal region B in the product widthwise direction $D_W$ is a region A.

The proximal region B is the region overlapping the side flaps 50, which is joined with the side flaps 50. The central region C is the region formed only with the base sheet 120 between the proximal region B and the hook sheet region D. The hook sheet region D is the region provided with the hook sheet 110.

In the present embodiment, the KES bending rigidity value of the fastening tape 100 in the product widthwise direction $D_W$ and the product longitudinal direction $D_L$ that is perpendicular to the product widthwise direction $D_W$ is set to 1.63 gf·cm²/cm or less.

The bending rigidity value (unit: gf·cm²/cm) of the proximal region B is preferably larger than the bending rigidity value in the region A. Furthermore, the bending rigidity value in the hook sheet region D is preferably larger than the bending rigidity value in the central region C, and the bending rigidity value in the proximal region B is preferably larger than the bending rigidity value in the central region C.

Furthermore, the width of the fastening tape 100 in the product longitudinal direction is tapered as it goes down from the proximal region B towards the tip region E. In the present embodiment, the difference d between the width of the proximal region B along the product longitudinal direction $D_L$ at the outer end in the product widthwise direction $D_W$, and the width of the hook sheet region D along the product longitudinal direction $D_L$ at the outer end in the product widthwise direction $D_W$ is set to 4 mm to 8 mm. If the proximal region B of the fastening tape 100 is made very broad, the proximal region might not match the roundness of the wearer's body, in the view of rigidity and shape. When the difference in the width exceeds 8 mm, the dimensions become too large relative to the round shape in the waist flank portion or the inguinal portion around the legs, resulting in excess diaper cloth. Therefore, the proximal region B obstructs the trailing of the fastening tape 100 along the body. On the other hand, when the difference is less than 4 mm, the accurate manufacturing in the process of cutting the fastening tape 100 into the appropriate shape becomes difficult.

The engagement strength of the fastening tape 100 having such a structure is set to 0.3 N/30 mm or more, and 1.5 N/30 mm or less. Furthermore, the bending rigidity value in the direction in which the surface of the base sheet 120 of the fastening tape 100 comes close is smaller than the bending rigidity value in the direction in which the surface of the hook sheet 110 of the fastening tape 100 comes close.

Figure 5:
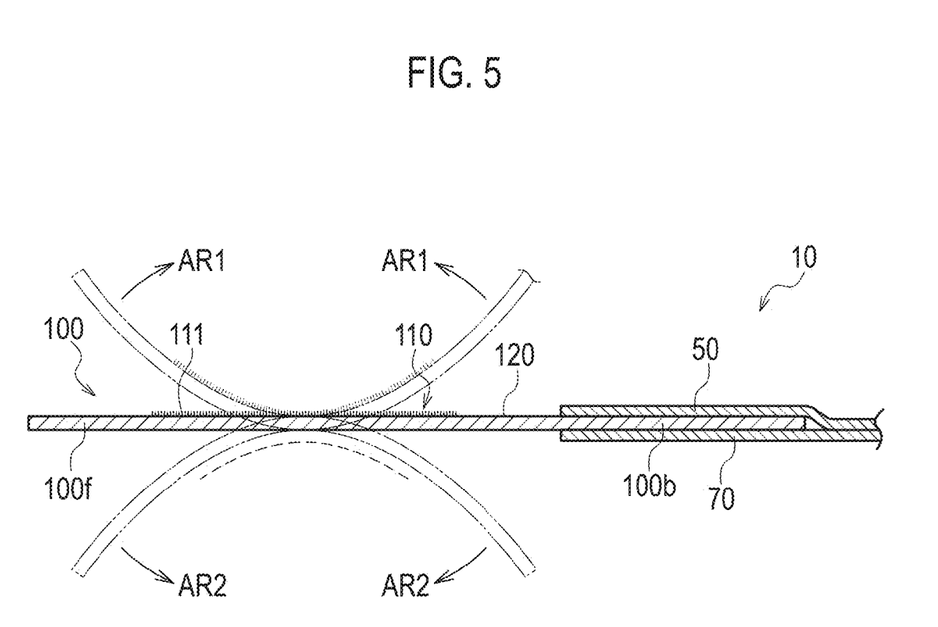
FIG. 5 is a diagram that schematically illustrates the state of deformation of the fastening tape 100 according to the embodiment of the present invention.

FIG. 5 is a diagram that schematically illustrates the state of deformation of the fastening tape 100. As illustrated by the lower bar in FIG. 5, the direction in which the surface of the hook sheet 110 of the fastening tape 100 comes close implies the direction in which the surface provided with the engagement hooks 111 is curved to come close (AR1 in the figure). The bending in such a direction is hereinafter appropriately referred to as "inner bending".

Furthermore, as illustrated by the lower bar in FIG. 5, the direction in which the surface of the base sheet 120 comes close implies the direction in which the surface of the base sheet 120 at the side that is not provided with the hook sheet 110 bows along the length and comes close (AR2 in the figure). For convenience, the bending in such a direction is hereinafter referred to as "outer bending".

In order to achieve such a characteristic to the fastening tape 100, the density of arrangement of the engagement hooks 111 is increased. Specifically, the density of arrangement is more than 1800 ppi (pins/inch), and preferably more than 2800 ppi. Thus, the characteristic with which outer bending occurs easily can be provided. That is, by increasing the density of arrangement of the engagement hooks 111, it becomes difficult for inner bending to occur as compared to outer bending because of interference caused by the adjacent engagement hooks 111.

Furthermore, in several layers of nonwoven fabrics that forms the base sheet 120, the characteristic with which "outer bending" occurs easily can be similarly provided, even when the density of fibers of the nonwoven fabric provided at the side of the hook sheet 110 is reduced. In addition, when embossing is performed in a nonwoven fabric forming the base sheet 120, the characteristic with which "outer bending" occurs easily can be provided in the same way, by performing embossing in a convex pattern from the side of the surface of the base sheet 120 at the side that is not provided with the hook sheet 110. Alternatively, in several layers of nonwoven fabrics that forms the base sheet 120, the characteristic with which "outer bending" occurs easily can be provided in the same way, by reducing the thickness of the nonwoven fabric on the outer side (the side closer to the surface of the base sheet 120 at the side that is not provided with the hook sheet 110).

Furthermore, in the present embodiment, as illustrated in FIG. 1, an absorber existent region A1 in which the absorbent body 15 is arranged, and an absorber non-existent region A2 in which the absorbent body 15 is not arranged are formed in the skin contact surface side of the target tape 60.

The width W1 in the product longitudinal direction $D_L$ of the fastening tape 100 is more than the width W2 of the absorber existent region A1 in the product longitudinal direction $D_L$. It must be noted that the width W1 implies the maximum width in the product longitudinal direction $D_L$ of the portion in which the hook sheet 110 exists.

(4) Examples

Subsequently, examples of the present invention will be explained. Table 1 provides an overview of the configuration and test results of the fastening tape according to examples 1 through 3, and the fastening tape according to comparative examples 1 through 4 (hereinafter, appropriately abbreviated as examples and comparative examples).

TABLE 1

| unit | base sheet configuration | | KES | | |
| --- | --- | --- | --- | --- | --- |
| | one layer (inner side) g/m² | two layers (outer side) g/m² | bending rigidity value gf·cm²/cm | bending direction | tape unfastening test results |
| example 1 | 50 | 30 | 0.91 | OK | good |
| example 2 | 20 | 25 | 0.36 | OK | good |
| example 3 | 80 | 27 | 1.63 | OK | good |
| comparative example 1 | 30 | 50 | 0.91 | NG | OK |
| comparative example 2 | 27 | 80 | 1.63 | NG | bad |
| comparative example 3 | SB 90 | — | 3.25 | — | bad |
| comparative example 4 | SB 30 | — | 0.43 | — | — |

As described in Table 1, the base sheet 120 configured from two layers (inner side and outer side) of nonwoven fabrics was used. The inner side implies the hook sheet 110 side.

The bending rigidity value of the fastening tape was measured using the KES bending tester manufactured by KATO TECH Co., Ltd. Specifically, the B value was measured.

Specifically, the details of the KES method are explained in "The Standardization and Analysis of Hand Evaluation" 2nd Edition (The Hand Evaluation and Standardization Committee, the Textile Machinery Society of Japan, Issued on Jul. 10, 1980). Thus, a measurement method of each mechanical property is described only for measurement conditions related to the present measurement.

The KES bending rigidity value was measured using KES-FB2 manufactured by KATO TECH Co., Ltd. by fixing each sample between chucks (where the skin surface side (inner side) of the fastening tape of the diaper faces downwardly), bending up to maximum curvature+2.5 cm−1 towards the front, and then bending up to maximum curvature−2.5 cm−1 towards the back, and then returning to the origin. In Table 1, both the bending rigidity value in the product longitudinal direction $D_L$ and the bending rigidity value in the product widthwise direction $D_W$ were measured, and the larger value of the two is illustrated. As described in Table 1, the unfastening of the tape can further be prevented when the KES bending rigidity is 1.63 gf·cm²/cm or less.

In the test for confirming the bending direction (inner bending and outer bending), in the bending property relationship obtained by plotting the relationship between the bending moment M (gf·cm/cm) per unit area obtained from the above measurement and the curvature K (1/cm), the direction in which the sample bent more easily was checked by comparing the slope Bf of the curve obtained by plotting the bending moment M during bending towards the front with respect to the measurement stage and the slope Bb of the curve obtained by plotting the bending moment M during bending towards the back. Specifically, this implies that the smaller the value of the slope, the more easily bending occurs.

Furthermore, in the test, a sample in which the engagement strength of the fastening tape is between 0.5 and 0.7 N was used. The engagement strength was measured using an Autograph tester (AG-X10plus) manufactured by Shimadzu Corporation. Specifically, a sample in which 30-mm width of the hook sheet and the base sheet had been cut out from the fastening tape to be measured (if it is not possible to cut out a width of 30 mm, the result was judged through conversion per 30-mm width) was prepared. Similarly, a sample in which the target tape to which the fastening tape was locked had been cut out in a size larger than the hook sheet was prepared.

Next, a 700-g roller (85-mm diameter and 45-mm width) was rotated at a speed of 5 mm/min. along the direction of fixing and peeling the main fastening tape, and both samples were pressure-bonded. Both the pressure-bonded samples were set in the Autograph tester, and the engagement strength of both samples at a tension speed of 300 mm/min. was measured (unit: N/30 mm). At this time, the direction of pull was set such that the hook sheet surface makes an angle of 135° with the target tape surface. Also, the peeling direction of the hook sheet was considered as the main direction of fixing and peeling during the time of operation (fixing and peeling) of the fastening tape.

Although the following does not directly stem from the concerned samples, one finding shows that if the engagement strength of the fastening tape exceeds 1.5 N, the subjects of the study (mothers having the infants and toddlers) seemed to find it difficult to attach and detach the fastening tape. On the other hand, another finding was that: if the engagement strength is less than 0.3 N, the impression that is given is that it is difficult to engage the fastening tape on the disposable diaper main body, and though the fastening tape is not actually unfastened, one feels that the fastening tape is unfastened, which is not preferable.

As for the tape unfastening test results, a test was conducted by 50 subjects on total of 1,000 disposable diapers, and samples in which the unfastening of the fastening tape during the use of the disposable diaper did not occur even in a single diaper were considered as "Good" while samples in which the unfastening occurred in either one or two diapers were considered as "OK". Samples in which the unfastening occurred in three or more diapers were considered as "bad".

As illustrated in Table 1, due to a high bending rigidity value, the unfastening of the fastening tape occurred in the comparative example 3. Furthermore, as illustrated in the comparative example 4, if the bending rigidity value is smaller than 0.43 gf·cm²/cm, the fastening tape becomes too flexible, and even if the engagement strength is set in the range described above, the fastening tape is evaluated as "difficult to attach and detach".

(5) Operation and Effect

The engagement strength of the fastening tape 100 provided in the above disposable diaper 10 is set to 0.3 N/30 mm or more, and 1.5 N/30 mm or less. Therefore, the engagement strength of the fastening tape 100 is low, and fine adjustment of the position of installing the fastening tape 100 with respect to the target tape 60 becomes easy. Furthermore, the bending rigidity value in the direction in which the surface of the base sheet 120 of the fastening tape 100 comes close (outer bending) is smaller than the bending rigidity value in the direction in which the surface of the hook sheet 110 of the fastening tape 100 comes close (inner bending). Therefore, even when the engagement strength of the fastening tape 100 is reduced, if the outer bending of the fastening tape 100 is facilitated, then the fastening tape 100 can easily trail along the recessed wrinkles at the side of the body of the wearer that occur on the surface of the target tape 60 and are a major cause of unfastening of the fastening tape from the target tape 60, thus making it difficult for the fastening tape 100 to unfasten. Thus, adjustments can be made easily such that the fastening tape 100 does not over-tighten the waistline of the wearer, and also easily continues to run along the waistline.

That is, when inner bending occurs in the fastening tape 100 at the time of occurrence of wrinkles, with respect to the recessed wrinkles at the side of the body of the wearer that occur easily on the surface of the target tape 60 as a result of the movement of the wearer (such as during stooping and raising the leg), the contact area between the hook sheet 110 and the target tape 60 reduces and the fastening tape 100 can easily unfasten from the target tape 60, which is not preferable. On the other hand, even when outer bending occurs, the contact area between the hook sheet 110 and the target tape 60 is not reduced, and the hook sheet 110 can curve easily along with the target tape 60 (indicated by the dotted line in FIG. 5). Therefore, the unfastening of the fastening tape 100 from the target tape 60 even when outer bending occurs can be controlled further.

That is, the fastening tape 100 can be adjusted easily so that the waistline of the wearer is not over-tightened, and the fastening tape 100 can be made to run more appropriately along the shape of the waistline of the wearer. Furthermore, even when the engagement strength of the fastening tape 100 is reduced, the state in which it is difficult for the fastening tape 100 to unfasten can be obtained.

In the present embodiment, as illustrated in FIG. 4, the side flaps 50 and the fastening tape 100 satisfy the relationship that the bending rigidity value in the proximal region B>bending rigidity value in the region A, the bending rigidity value in the hook sheet region D>bending rigidity value in the central region C, and the bending rigidity value in the proximal region B>bending rigidity value in the central region C. Therefore, in order to run along the complex irregularity such as the waist flank portion and the inguinal portion around the legs of the wearer, rather than having a uniform rigidity, a portion with a low rigidity is provided, and by alternately repeating the region having a relatively high rigidity with a region having a low rigidity, the portion with a low rigidity becomes a cushioning unit that prevents the occurrence of wrinkles due to a local load making it difficult for the fastening tape 100 to unfasten from the target tape 60. Furthermore, rather than having all portions with a low rigidity, the portion close to the side flaps 50 (the proximal region B) and the hook sheet region D that is held frequently by the user while handling the fastening tape 100 have a certain rigidity which make handling easy when the fastening tape 100 is attached or detached.

In addition, the width of the fastening tape 100 in the product longitudinal direction $D_L$ is tapered as it goes down from the proximal region B towards the tip region E of the fastening tape 100. Therefore, trailing along the shape of the abdomen of the wearer, particularly, that of infants and toddlers, which is relatively protruding towards the front, becomes easy and the load exerted on the fastening tape 100 as a result of the movement of the wearer (particularly the movements involved in sitting and raising legs) reduces, thus making it difficult for the fastening tape 100 to unfasten.

In the present embodiment, the width W1 of the fastening tape 100 in the product longitudinal direction $D_L$ is more than the width W2 of the absorber existent region A1 in the product longitudinal direction $D_L$. Therefore, the rigidity of the absorbent body 15 can be used to more firmly engage the fastening tape 100 onto the target tape 60. As a result, it becomes difficult for the fastening tape 100 to unfasten from the target tape 60.

(6) Other Embodiments

So far, the present invention is disclosed through the above embodiment of the present invention. However, it should not be interpreted that the statements and drawings constituting a part of the present disclosure limit the present invention. From this disclosure, a variety of alternate embodiments, examples, and applicable techniques will become apparent to one skilled in the art.

For example, in the above embodiment, the width W1 of the fastening tape 100 in the product longitudinal direction $D_L$ is more than the width W2 of the absorber existent region A1 in the product longitudinal direction $D_L$, however, such a relationship need not necessarily be satisfied.

Furthermore, in the above embodiment, the side flaps 50 and the fastening tape 100 satisfied the relationship that the bending rigidity value in the proximal region B>bending rigidity value in the region A, the bending rigidity value in the hook sheet region D>bending rigidity value in the central region C, and the bending rigidity value in the proximal region B>bending rigidity value in the central region C, however, such a relationship need not necessarily be satisfied.

As described above, it is of course that the present invention includes various embodiments and the like not described here. Therefore, the technical range of the present invention is to be defined only by the inventive specific matter according to the adequate claims from the above description.

REFERENCE SIGNS LIST

10 . . . Disposable diaper
15 . . . Absorbent body
20 . . . Front waistline unit
30 . . . Crotch unit
35 . . . Absorber
40 . . . Back waistline unit
50 . . . Side flaps
55 . . . Leg elastic members
60 . . . Target tape
70 . . . Backsheet
100 . . . Fastening tape
110 . . . Hook sheet
111 . . . Engagement hook
111a . . . Pillar unit
111b . . . Umbrella unit
115 . . . Base sheet unit
120 . . . Base sheet

The invention claimed is:
1. A disposable diaper, comprising:
a vertically long absorbent body formed by a front waistline unit, a back waistline unit, and a crotch unit, and including a liquid-retentive absorber;

side flaps provided at least at a part of side edges of the absorbent body in a product widthwise direction of the disposable diaper; and a fastening tape attached to one of the side flaps, extending outwardly in the product widthwise direction from one of the front waistline unit and the back waistline unit, and configured to be fastened to a remaining one of the front waistline unit and the back waistline unit; wherein the fastening tape has
  a base sheet, and
  a hook sheet provided with a plurality of engagement hooks and fixed on a surface of the base sheet,
the fastening tape has
  a tip region not provided with the hook sheet, and
  a hook sheet region provided with the hook sheet and inwardly adjacent to the tip region in the product widthwise direction,
an engagement strength of the fastening tape is 0.3 N/30 mm or more, and 1.5 N/30 mm or less,
a density of the engagement hooks is more than 1800 pins/inch,
the base sheet is formed of a first nonwoven fabric layer configured to face toward a wearer's garment and a second nonwoven fabric layer configured to face toward the wearer's skin,
a thickness of the first nonwoven fabric layer is less than a thickness of the second nonwoven fabric layer,
the fastening tape has (i) a first bending rigidity value when the fastening tape is bent in a first direction from the hook sheet toward the base sheet to form a central apex closer to a wearer's garment than edges of the fastening tape, and (ii) a second bending rigidity value when the fastening tape is bent in a second direction from the base sheet toward the hook sheet to form a central apex closer to the wearer's skin than the edges of the fastening tape, and
the first bending rigidity value of the fastening tape is greater than the second bending rigidity value of the fastening tape.

2. The disposable diaper according to claim 1, wherein a KES bending rigidity value of the fastening tape in the product widthwise direction and in a product longitudinal direction that is perpendicular to the product widthwise direction is 1.63 gf·cm$^2$/cm or less.

3. The disposable diaper according to claim 1, wherein the fastening tape further includes:
  a proximal region overlapping the side flaps; and
  a central region formed only with the base sheet and located between the proximal region and the hook sheet region,
a bending rigidity value in the proximal region is larger than a bending rigidity value in a region of said one of the side flaps that is adjacent to the proximal region,
a bending rigidity value in the hook sheet region is larger than a bending rigidity value in the central region, and
the bending rigidity value in the proximal region is larger than the bending rigidity value in the central region.

4. The disposable diaper according to claim 3, wherein a width of the fastening tape in a product longitudinal direction perpendicular to the product widthwise direction is tapered from the proximal region towards the tip region of the fastening tape.

5. The disposable diaper according to claim 4, wherein the proximal region has a proximal edge in the product widthwise direction, the hook sheet region has a distal edge in the product widthwise direction,
a difference between a width of the proximal edge of the proximal region along the product longitudinal direction, and a width of the distal edge of the hook sheet region along the product longitudinal direction is between 4 mm and 8 mm.

6. The disposable diaper according to claim 1, further comprising a target tape configured to engage with the hook sheet of the fastening tape,
wherein
  the target tape, at a skin contact surface side thereof, includes:
    an absorber existent region in which the absorbent body overlaps the target tape, and
    an absorber non-existent region in which the absorbent body does not overlap the target tape, and
  a width of the fastening tape in a product longitudinal direction perpendicular to the product widthwise direction is more than a width of the absorber existent region in the product longitudinal direction.

7. The disposable diaper according to claim 1, wherein the density of the engagement hooks is more than 2800 pins/inch.

8. The disposable diaper according to claim 5, wherein a KES bending rigidity value of the fastening tape in the product widthwise direction and in the product longitudinal direction that is perpendicular to the product widthwise direction is 1.63 gf·cm$^2$/cm or less.

9. The disposable diaper according to claim 8, wherein the density of the engagement hooks is more than 2800 pins/inch.

10. The disposable diaper according to claim 9, further comprising a target tape configured to engage with the hook sheet of the fastening tape,
wherein
  the target tape, at a skin contact surface side thereof, includes:
    an absorber existent region in which the absorbent body overlaps the target tape, and
    an absorber non-existent region in which the absorbent body does not overlap the target tape, and
  a width of the fastening tape in the product longitudinal direction is more than a width of the absorber existent region in the product longitudinal direction.

11. A disposable diaper, comprising:
a vertically long absorbent body formed by a front waistline unit, a back waistline unit, and a crotch unit, and including a liquid-retentive absorber;
side flaps provided at least at a part of side edges of the absorbent body in a product widthwise direction of the disposable diaper; and
a fastening tape attached to one of the side flaps, extending outwardly in the product widthwise direction from one of the front waistline unit and the back waistline unit, and configured to be fastened to a remaining one of the front waistline unit and the back waistline unit; wherein the fastening tape has
  a base sheet, and
  a hook sheet provided with a plurality of engagement hooks and fixed on a surface of the base sheet,
the fastening tape has
  a tip region not provided with the hook sheet, and
  a hook sheet region provided with the hook sheet and inwardly adjacent to the tip region in the product widthwise direction, an engagement strength of the fastening tape is 0.3 N/30 mm or more, and 1.5 N/30 mm or less, a density of the engagement hooks is more than 1800 pins/inch, the base sheet is formed of a first nonwoven fabric layer configured to face toward a wearer's garment and a second nonwoven fabric layer configured to face toward the wearer's skin, a density of fibers of the second nonwoven fabric layer is less than a density of fibers of the first nonwoven fabric layer, the fastening tape has (i) a first bending rigidity value when the fastening tape is bent in a first direction from the hook sheet toward the base sheet to form a central apex closer to the wearer's garment than edges of the fastening tape, and (ii) a second bending rigidity value when the fastening tape is bent in a second direction from the base sheet toward the hook sheet to form a central apex closer to the wearer's skin than the edges of the fastening tape, and the first bending rigidity value of the fastening tape is greater than the second bending rigidity value of the fastening tape.

12. The disposable diaper according to claim 11, wherein the fastening tape further includes:

a proximal region overlapping the side flaps; and a central region formed only with the base sheet and located between the proximal region and the hook sheet region, a bending rigidity value in the proximal region is larger than a bending rigidity value in a region of said one of the side flaps that is adjacent to the proximal region, a bending rigidity value in the hook sheet region is larger than a bending rigidity value in the central region, and the bending rigidity value in the proximal region is larger than the bending rigidity value in the central region.

13. The disposable diaper according to claim 12, wherein a width of the fastening tape in a product longitudinal direction perpendicular to the product widthwise direction is tapered from the proximal region towards the tip region of the fastening tape.

14. The disposable diaper according to claim 13, wherein the proximal region has a proximal edge in the product widthwise direction, the hook sheet region has a distal edge in the product widthwise direction, a difference between a width of the proximal edge of the proximal region along the product longitudinal direction, and a width of the distal edge of the hook sheet region along the product longitudinal direction is between 4 mm and 8 mm.

15. The disposable diaper according to claim 14, wherein a KES bending rigidity value of the fastening tape in the product widthwise direction and in the product longitudinal direction that is perpendicular to the product widthwise direction is 1.63 gf·cm$^2$/cm or less.

16. The disposable diaper according to claim 15, wherein the density of the engagement hooks is more than 2800 pins/inch.

17. The disposable diaper according to claim 16, further comprising a target tape configured to engage with the hook sheet of the fastening tape, wherein the target tape, at a skin contact surface side thereof, includes:

an absorber existent region in which the absorbent body overlaps the target tape, and an absorber non-existent region in which the absorbent body does not overlap the target tape, and a width of the fastening tape in the product longitudinal direction is more than a width of the absorber existent region in the product longitudinal direction.

* * * * *